US007004943B2

(12) United States Patent
Ferrante et al.

(10) Patent No.: US 7,004,943 B2
(45) Date of Patent: Feb. 28, 2006

(54) DEVICES, SYSTEMS, AND METHODS FOR PLACING AND POSITIONING FIXATION ELEMENTS IN EXTERNAL FIXATION SYSTEMS

(75) Inventors: Joseph Ferrante, Bartlett, TN (US); Ed Austin, Bartlett, TN (US); Anthony James, Bartlett, TN (US)

(73) Assignee: Smith & Nephew, Inc., Memphis, TN (US)

( * ) Notice: Subject to any disclaimer, the term of this patent is extended or adjusted under 35 U.S.C. 154(b) by 182 days.

(21) Appl. No.: 10/172,654

(22) Filed: Jun. 14, 2002

(65) Prior Publication Data

US 2003/0149430 A1   Aug. 7, 2003

Related U.S. Application Data

(63) Continuation-in-part of application No. 10/067,052, filed on Feb. 4, 2002.

(51) Int. Cl.
  *A61B 17/56*  (2006.01)
  *A61F 4/00*  (2006.01)
  *A61F 5/04*  (2006.01)
  *A61F 2/00*  (2006.01)

(52) U.S. Cl. .......................................... 606/59; 606/96
(58) Field of Classification Search ................. 606/53, 606/54, 59, 79, 80, 86, 87, 96, 98, 102, 103, 606/104, 57, 60, 61; 403/137, 138, 384, 403/385, 396; 248/229.1, 229.14, 229.2, 248/229.26, 288.11
See application file for complete search history.

(56) References Cited

U.S. PATENT DOCUMENTS

| 554,284 A | 2/1896 | Lorang |
|---|---|---|
| 575,631 A | 1/1897 | Brooks |
| 1,271,792 A | 7/1918 | Standish |
| 1,563,242 A | 11/1925 | Tweit |
| 2,250,417 A | 7/1941 | Ettinger |
| 2,251,209 A | 7/1941 | Stader |
| 2,346,346 A | 4/1944 | Anderson |
| 2,391,537 A | 12/1945 | Anderson |
| 2,391,693 A | 12/1945 | Ettinger |
| 2,393,694 A | 1/1946 | Kirschner |
| 2,393,831 A | 1/1946 | Stader |

(Continued)

FOREIGN PATENT DOCUMENTS

CH           303453           5/1952

(Continued)

OTHER PUBLICATIONS

International Search Report in related Application No. PCT/US03/02712.

(Continued)

*Primary Examiner*—Eduardo C. Robert
*Assistant Examiner*—Anuradha Ramana
(74) *Attorney, Agent, or Firm*—Kilpatrick Stockton LLP

(57) ABSTRACT

Methods, systems, and devices according to this invention provide drill guides for optimal placement of fixation elements, such as half pins, into a patient's bone. According to one embodiment, a collar frame with a collar adapted to receive a bar of an orthopedic external fixation system such that the collar may be moved linearly or rotationally about the bar is coupled to a guide frame including a bore through which a fixation element of the external fixation system may be inserted. The coupling between the collar frame and the guide frame allows for them to rotate about at least one axis relative to each other. In one embodiment, the collar frame and the guide frame may rotate about three axes relative to each other.

60 Claims, 11 Drawing Sheets

U.S. PATENT DOCUMENTS

| | | | |
|---|---|---|---|
| 2,427,128 A | | 9/1947 | Ettinger |
| 2,774,271 A | | 12/1956 | Mano |
| 2,876,027 A | | 3/1959 | Sulmonetti |
| 2,932,029 A | | 4/1960 | De Nicolo |
| 3,044,512 A | | 7/1962 | Jones |
| 3,154,331 A | | 10/1964 | Engelhardt |
| 3,195,380 A | | 7/1965 | Bicks |
| 3,509,882 A | | 5/1970 | Blake |
| 3,828,791 A | | 8/1974 | Santos |
| 3,961,854 A | | 6/1976 | Jaquet |
| 4,135,505 A | | 1/1979 | Day |
| 4,170,990 A | * | 10/1979 | Baumgart et al. ............ 606/78 |
| 4,187,840 A | | 2/1980 | Watanabe |
| 4,227,826 A | | 10/1980 | Conrad |
| 4,364,381 A | | 12/1982 | Sher et al. |
| 4,475,546 A | | 10/1984 | Patton |
| 4,483,334 A | | 11/1984 | Murray |
| RE31,809 E | | 1/1985 | Danieletto et al. |
| 4,548,199 A | | 10/1985 | Agee |
| 4,570,625 A | | 2/1986 | Harris et al. |
| 4,611,586 A | | 9/1986 | Agee et al. |
| 4,620,533 A | | 11/1986 | Mears |
| 4,635,634 A | | 1/1987 | Santos |
| 4,666,109 A | * | 5/1987 | Fallon et al. ................. 248/50 |
| 4,696,293 A | | 9/1987 | Ciullo |
| 4,700,437 A | | 10/1987 | Hoshino |
| 4,730,608 A | * | 3/1988 | Schlein ........................ 606/57 |
| 4,785,694 A | | 11/1988 | Burmester |
| 4,848,368 A | | 7/1989 | Kronner |
| 4,922,856 A | | 5/1990 | Sweeney, Jr. |
| 4,998,935 A | | 3/1991 | Pennig |
| 5,062,844 A | | 11/1991 | Jamison et al. |
| 5,152,280 A | | 10/1992 | Danieli |
| 5,160,335 A | | 11/1992 | Wagenknecht |
| 5,167,725 A | | 12/1992 | Clark et al. |
| 5,207,676 A | | 5/1993 | Canadell et al. |
| 5,219,349 A | | 6/1993 | Krag et al. |
| 5,304,177 A | | 4/1994 | Pennig |
| 5,376,090 A | | 12/1994 | Pennig |
| 5,403,313 A | | 4/1995 | Lin |
| 5,405,347 A | | 4/1995 | Lee et al. |
| RE34,985 E | | 6/1995 | Pennig |
| 5,429,637 A | | 7/1995 | Hardy |
| 5,437,666 A | | 8/1995 | Tepic et al. |
| 5,443,465 A | | 8/1995 | Pennig |
| 5,451,225 A | | 9/1995 | Ross, Jr. et al. |
| 5,451,226 A | | 9/1995 | Pfeil et al. |
| 5,507,760 A | | 4/1996 | Wynne et al. |
| 5,545,162 A | | 8/1996 | Huebner |
| 5,586,983 A | | 12/1996 | Sanders et al. |
| 5,624,447 A | * | 4/1997 | Myers .......................... 606/96 |
| 5,658,283 A | | 8/1997 | Huebner |
| 5,662,648 A | | 9/1997 | Faccioli et al. |
| 5,662,649 A | | 9/1997 | Huebner |
| 5,662,650 A | | 9/1997 | Bailey et al. |
| 5,683,389 A | | 11/1997 | Orsak |
| 5,690,633 A | * | 11/1997 | Taylor et al. ................. 606/73 |
| 5,702,389 A | | 12/1997 | Taylor et al. |
| 5,707,370 A | | 1/1998 | Berki et al. |
| 5,709,685 A | | 1/1998 | Dombrowski et al. |
| 5,728,095 A | | 3/1998 | Taylor et al. |
| 5,728,096 A | * | 3/1998 | Faccioli et al. ............... 606/54 |
| 5,741,252 A | | 4/1998 | Mazzio et al. |
| 5,743,898 A | | 4/1998 | Bailey et al. |
| 5,746,741 A | | 5/1998 | Kraus et al. |
| 5,752,954 A | | 5/1998 | Mata et al. |
| 5,788,695 A | | 8/1998 | Richardson |
| 5,810,817 A | | 9/1998 | Roussouly et al. |
| 5,823,486 A | * | 10/1998 | Smith et al. ................ 248/104 |
| 5,827,282 A | | 10/1998 | Pennig |
| 5,891,143 A | | 4/1999 | Taylor et al. |
| 5,891,144 A | | 4/1999 | Mata et al. |
| 5,931,837 A | | 8/1999 | Marsh et al. |
| 5,968,043 A | * | 10/1999 | Ross et al. .................... 606/56 |
| 5,971,984 A | | 10/1999 | Taylor et al. |
| 5,976,134 A | | 11/1999 | Huebner |
| 6,010,501 A | | 1/2000 | Raskin et al. |
| 6,024,745 A | | 2/2000 | Paccioli et al. |
| 6,030,386 A | | 2/2000 | Taylor et al. |
| 6,036,691 A | | 3/2000 | Richardson |
| 6,066,142 A | * | 5/2000 | Serbousek et al. ............ 606/96 |
| 6,080,153 A | | 6/2000 | Mata et al. |
| 6,129,727 A | | 10/2000 | Austin et al. |
| 6,168,595 B1 | | 1/2001 | Durham et al. |
| 6,171,308 B1 | | 1/2001 | Bailey et al. |
| 6,203,575 B1 | | 3/2001 | Farey |
| 6,217,577 B1 | | 4/2001 | Hofmann |
| 6,221,072 B1 | | 4/2001 | Termaten |
| 6,238,400 B1 | * | 5/2001 | Bays ........................... 606/96 |
| 6,342,054 B1 | | 1/2002 | Mata |
| 6,386,786 B1 | * | 5/2002 | Perlman et al. ............... 403/90 |
| 6,461,358 B1 | | 10/2002 | Faccioli et al. |
| 6,491,694 B1 | | 12/2002 | Orsak |
| 6,503,340 B1 | | 1/2003 | Gold et al. |
| 6,613,049 B1 | * | 9/2003 | Winquist et al. ............... 606/59 |
| 6,616,664 B1 | * | 9/2003 | Walulik et al. ................ 606/57 |
| 6,709,433 B1 | * | 3/2004 | Schoenefeld ................. 606/57 |
| 2002/0026190 A1 | | 2/2002 | Walulik et al. |
| 2003/0149429 A1 | | 8/2003 | Ferrante et al. |

FOREIGN PATENT DOCUMENTS

| | | |
|---|---|---|
| CH | 02 709/94-3 | 9/1994 |
| DE | 375 151 | 5/1923 |
| DE | 1 935 977 | 2/1971 |
| DE | 1 603 999 | 5/1971 |
| DE | 27 45 504 A1 | 4/1979 |
| DE | 38 05 178 A1 | 8/1989 |
| DE | 38 23 746 A1 | 1/1990 |
| DE | 91 03 480.9 | 6/1991 |
| DE | 42 38 582 A1 | 5/1994 |
| DE | 295 12 917 U1 | 11/1995 |
| EP | 0 524 441 A1 | 6/1992 |
| EP | 0 611 007 A1 | 8/1994 |
| EP | 0 700 664 A1 | 3/1996 |
| EP | 1 021 992 A2 | 7/2000 |
| FR | 2 665 353 A | 2/1992 |
| NO | 25934 | 6/1915 |
| SU | 167008 | 11/1965 |
| SU | 1491-492 A1 | 8/1986 |
| SU | 1572590 A1 | 6/1990 |
| WO | WO 88/01152 | 2/1988 |
| WO | WO 88/03395 | 5/1988 |
| WO | WO 94/18898 | 9/1994 |
| WO | WO 96/12443 | 5/1996 |
| WO | WO 97/10775 | 3/1997 |
| WO | WO 97/16128 | 5/1997 |
| WO | WO 98/36698 | 8/1998 |
| WO | WO 99/22661 | 5/1999 |
| WO | WO 99/29247 | 6/1999 |
| WO | WO 00/40163 | 7/2000 |
| WO | WO 03/065911 | 8/2003 |

OTHER PUBLICATIONS

International Search Report in related Application No. PCT/US03/18067.

Patent Abstracts of Japan, vol. 017, No. 270 (C-1063), May 26, 1993 & JP 05 007604 A (Nagano Keiki Seisakusho), Jan. 19, 1993.

Agee, "External Fixation: Technical Advances Based Upon Multiplanar Ligamentotaxis," *Orthopedic Clinics of North America*, 24(2) (Apr. 1993).

Hoffmann II External Fixation System, 3 pages, (Oct. 15, 2001) http://www.osteonics.com/howmedica/products/frames/prod2p.10.htm.

Search Report for European patent EP 92 11 0526.

Smith & Nephew Brochure entitled "Only from Smith & Nephew The Original Ilizarov System," six pages (Jan. 1999).

International Search Report in related Application No. PCT/US03/39307.

"Epiphyseal Distraction Hemichondrodiatasis," by Roberto Aldergheri, et al., *Clinical Orthopaedics and Related Research*, No. 241, pp. 128-136, Apr. 1989.

"Use of an Articulated External Fixator for Fractures of the Tibial Plafond," *The Journal of Bone and Joint Surgery*, pp. 1498-1509, 1995.

Articulated External Fixation of Tibial Pilon Fractures: Effects on Ankle and Fragment Kinematics by D. C. Fitzpatrick, et al., 40th Annual Meeting, Orthopaedic Research Society, Feb. 21-24, 1994, New Orleans, Louisiana, one page.

ORTHOFIX Brochure entitled "Ankle Fusion Technique," one page, undated.

ORTHOFIX Brochure entitled "Arthrodiatasis Articulated Joint Distraction" by Dr. G. Trivella and Prof. M. Saleh, 8 pages (undated).

ORTHOFIX Operative Technique Brochure by Dr. J. L. Marsh and Dr. F. Lavini entitled "Distal Tibial and Pilon Fractures with the Radiolucent Ankle Clamp," pp. 1-21 (undated).

ORTHOFIX Operative Technique Brochure entitled "Distal Tibial and Pilon Fractures," by Dr. J. L. Marsh and Dr. F. Lavini, pp. 1-20, Oct. 16, 2002.

*Orthopedics Today*, vol. 14, No. 11, "Swedish cartilage replart study offers hope, but more research is needed," pp. 1 and 43, Nov. 1994.

* cited by examiner

DEVICES, SYSTEMS, AND METHODS FOR PLACING AND POSITIONING FIXATION ELEMENTS IN EXTERNAL FIXATION SYSTEMS

This application is a continuation-in-part of U.S. application Ser. No. 10/067,052, filed Feb. 4, 2002, now pending, entitled "External Fixation System," the entire contents of which are hereby incorporated by reference.

FIELD OF THE INVENTION

This invention relates generally to methods, systems, and devices for orthopedic external fixation and more particularly to methods, systems, and devices for use with external fixation systems for placing fixation elements, such as half pins, in a patient's bone.

BACKGROUND OF THE INVENTION

Surgeons use external fixation systems regularly to treat certain bone-related injuries or conditions, such as acute fractures of the skeleton, soft tissue injuries, delayed union of the skeleton when bones are slow to heal, nonunion of the skeleton when bones have not healed, malunion of broken or fractured bones, congenital deformities resulting in malposition of bone, and bone lengthening, widening, or twisting. Treatment of these conditions often includes stabilization and reduction using an external fixation system. These systems may include a frame comprised of one or more of fixation components and one or more fixation elements.

As used herein, fixation component refers to a device for positioning one or more parts of an external fixation system, and fixation element refers to one or more of a bar, rod, wire or pin used in an external fixation system. Wires may be threaded, beaded, or smooth, and pins may be threaded or smooth. Generally, one or more bone pins or wires are inserted into the tissue and bone and then the remainder of the fixation system is assembled. It is often important that a surgeon is able to place the external fixation system on the patient and then reduce the fracture in an expedited manner. Fracture patterns are infinite and may require the fixation system to move in multiple planes simultaneously in order to stabilize and reduce the fracture properly.

Current external fixation system designs vary, but generally include a mechanism for attaching at least one fixation element to a fixation component to form a construct, or frame, to support a fracture. In general, at least one pin or wire is drilled into the bone, and often more than two pins or wires are drilled into the bone. Bone pins typically have one end that is either or both self-drilling and self-tapping, and have a diameter sufficient to resist bending. Bone wires are generally smaller in diameter. Bone pins or wires may be drilled completely through the bone, exiting the skin on the opposite side of the bone, called "transfixation pins," or may extend through the bony skeleton and out only one side of the limb, called "half pins."

Current fixation components generally either connect a bar to a bar, a bar to a wire, or a bar to a pin. The frame of an external fixation system may include unilateral bars, which extend along the side of a patient's body, or circumferential or half rings, which encircle a patient's body member entirely or in part. Systems designed to use a circumferential ring or half ring include the ILIZAROV® brand system and the SPATIAL FRAMEO® brand system. The SPATIAL FRAME® brand system is described in U.S. Pat. No. 5,702,389, which is hereby incorporated by reference. Generally, circumferential and half rings have a rectangular cross-section.

When stabilizing and reducing a fracture using an external fixation system, it is important to properly align the bone fragments. Such alignment requires a fixation component that securely joins the pins and wires to the bars, but that is readily adjustable. In many cases, initially, one pin is inserted below the fracture and another pin is inserted above the fracture. The surgeon then attaches a fixation component to each pin, bridging the fixation components together with rods, or bars. These bars form the frame of the external fixation system. As additional fixation components are added to the system in different planes, the frame become less adjustable. Current fixation systems permit a surgeon to choose the positioning of only two fixation components because after placement of two components, additional fixation components will only fit into set positions. During a procedure, it is often necessary to further reduce a fracture, which requires removal of the bars (and loss of positioning) and then replacement of the bars in the frame. Thus, additional reduction is difficult to achieve and requires reestablishment of optimal position. Current systems are also highly dependent on accurate pin or wire placement. For example, if the pins or wires are angled incorrectly, the frame cannot be properly constructed.

One current external fixation component design includes two clamps that rotate in one plane to allow limited manipulation of the external fixation component. One jaw of each clamp of this design includes a toothed chip mechanism that has a surface with teeth similar to a poker chip. The teeth mate and lock when compressed, and thereby resist rotation in one plane after the clamps are in place. This poker chip design requires that the two fixation elements retained by the component are parallel to each other in at least one plane that is parallel to the poker chip surface, so that the angular relationship between the two fixation elements is always zero in that plane. Therefore, this system requires a parallel plane between the pin or wire and bar (or between two bars) for each fixation component. This requirement limits the system, as the positioning of each clamp is inhibited. Similar to other current designs, this design becomes substandard when several fixation components are used because it becomes constrained.

In addition, the clamps of many current designs are adjacent a central shaft and are both locked upon tightening of a single screw, further constraining the system. Many current designs also allow for placement of the pins in the pin clamp of a fixation element only from the side and require a bent bar for placement of the system proximate the patient, if it is necessary to conform the system to the patient's anatomy. In addition, current designs use compression to hold the bar or pin in place, and may allow dislodgement of the pin or bar upon application of a great amount of pressure to the system when being placed.

With regard to the placement of pins or wires subsequent to the placement of the initial two pins or wires, current designs require pins or wires to be placed through a fixation component that is already attached to a bar or rod. In other words, the third and any subsequent fixation components must first be secured to the bar or rod of the frame, and the pin or wire must then be placed, or pre-drilled, through the fixation component before insertion into the patient's skin and bone. The fixation components dictate the pin position because the fixation components do not have the number of degrees of freedom that is required for optimal pin placement. This limits position of both the pin and the fixation component and is a significant disadvantage because the pin may be placed in a non-optimal position.

Other prior art designs include circumferential rings or half rings, such as those in the ILIZAROV® and SPATIAL FRAME® brand systems. These specialized systems are often used for reduction of a fracture of the proximal tibia or distal femur. Generally, wires connected to half rings are used to stabilize a fracture. These specialized systems do not cooperate with general external fixation systems, and must be used separately.

Thus, there is a need for an external fixation system that provides a greater degree of freedom of rotation of the fixation components and therefore a more flexible frame construct, sequential locking of capture members, allowing greater adjustability, and cooperation with specialized fixation systems.

There is also a need for a drill guide that allows fixation elements to be placed into the bone for optimal positioning of third and subsequent fixation elements of an external fixation system and such that fixation components will properly couple to the fixation elements.

SUMMARY OF THE INVENTION

An external fixation system according to one embodiment of this invention allows manipulation of an external fixation component in any plane independent of the number of fixation components used, which is provided by the ability of the fixation component to rotate in multiple planes. Further, an improved fixation component according to one embodiment of this invention provides an external fixation system that does not bind or become constricted when numerous fixation components are used, providing the surgeon a stable system that is adjustable. One embodiment of a fixation component according to this invention includes two capture members, each adapted to receive a fixation element. The capture members are coupled such that one capture member is capable of rotation in three axes relative to the other capture member and wherein the coupling is adapted to secure the first and second capture members from rotation with a single activation.

A drill guide according to an exemplary embodiment of this invention allows for optimal placement of fixation elements into a patient's bone. According to one embodiment, a collar frame includes a collar adapted to receive a bar of an external fixation system such that the collar may be moved linearly or rotationally about the bar. A guide frame, including a bore through which a fixation element, such as a pin or wire, of the external fixation system may be inserted, is coupled to the collar frame such that the guide frame and the collar frame may rotate about at least one axis relative to each other. A drill, drill bit, depth gauge, or tissue sleeve may also be inserted through the bore of the guide frame. In one embodiment, the guide frame and collar frame may rotate about three axes relative to each other.

In one embodiment, the bore of a guide frame may receive a tissue or drill sleeve that includes a channel through which a fixation element may be inserted. The tissue sleeve may assist in pushing soft tissue away from the end of a fixation element as the fixation element is placed into the patient's bone. In one embodiment, a drill guide is designed to mimic the positioning and rotational freedom of an embodiment of a fixation component according to the invention.

An embodiment of a method according to the invention includes using a drill guide to place a third or subsequent fixation element into a patient's bone as part of an external fixation system. The drill guide is slipped onto a bar of the external fixation system and moved axially or rotationally to the desired position to place the fixation element into the bone. The fixation element is inserted through a bore in the drill guide and placed into the patient's bone. The drill guide is removed from the bar, and a fixation component is used to couple the fixation element to the bar.

DETAILED DESCRIPTION OF THE INVENTION

Figure 1:
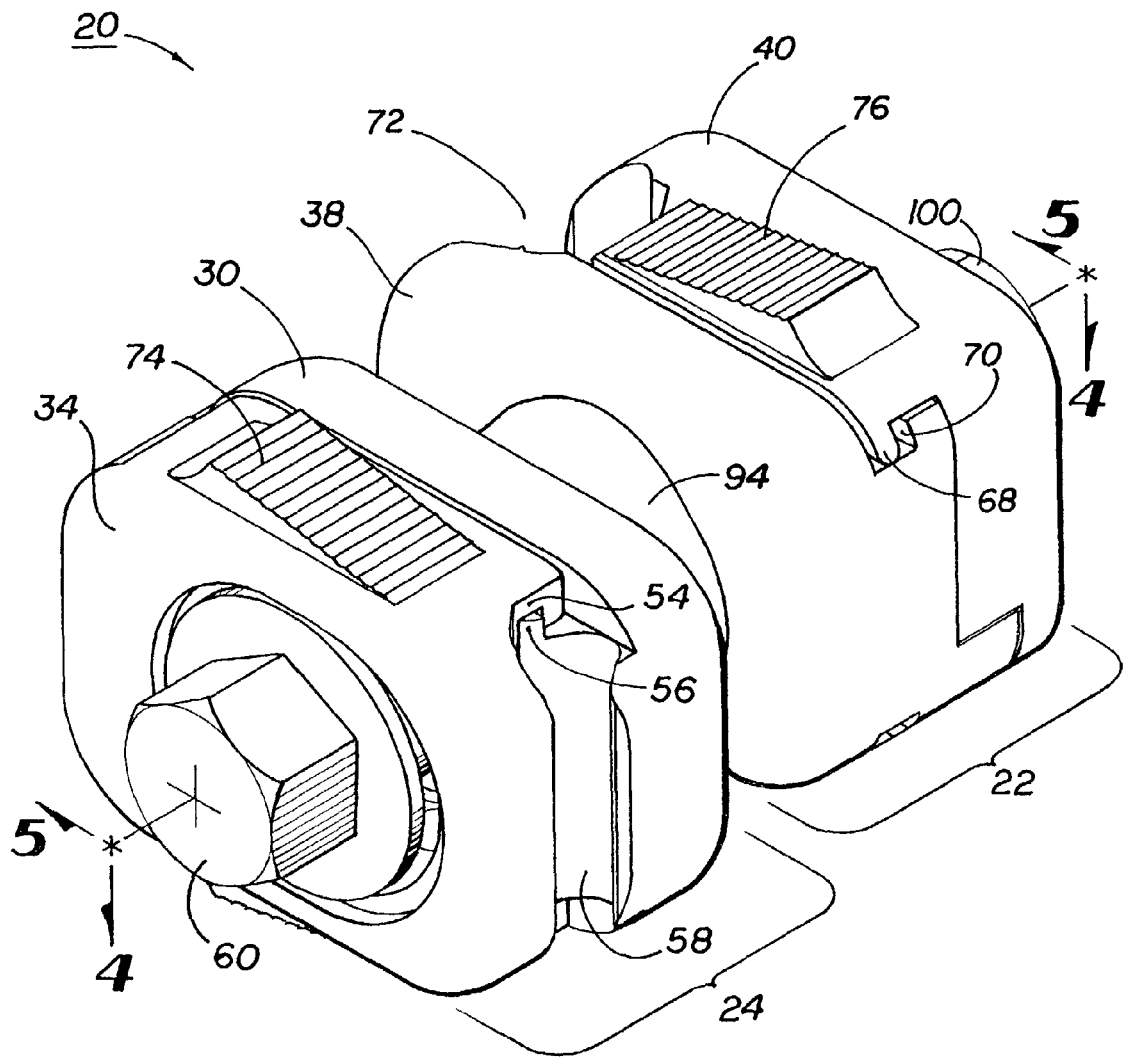
FIG. 1 is a perspective view of a fixation component according to one embodiment of this invention.

Methods, systems and devices according to this invention seek to provide improved external fixation, including an improved fixation component allowing an increase in freedom of rotation, independent locking of capture members, a more stable, yet more flexible frame, and cooperation with specialized fixation systems. External fixation systems according to embodiments of this invention may include fixation components designed to retain one or more fixation elements. In general, the fixation components either connect a bar to a bar; a bar to a pin; a bar to a wire; or a bar to a circumferential or half ring. Each fixation component generally includes two capture members, and each capture member includes a base and a head. Methods, systems, and devices according to this invention also provide drill guides for optimal placement of fixation elements into a patient's bone, as discussed in further detail below.

One embodiment of a fixation component according to this invention includes a first capture member and a second capture member connected by a joint. Each capture member includes a channel, which allows attachment of a fixation element from the side. Prior to being locked down, each fixation element can slide (back and forth) and rotate within the channel providing two degrees of freedom between the fixation element and the capture member. The first and second capture members are connected by a joint that allows each capture member to rotate with respect to the other capture member. The joint also allows rotation of up to 50° in any plane (25° each way). In one embodiment, angulation is limited to 50° due to profile height constraints. However, in another embodiment more angulation may be provided. Thus, each capture member is provided three degrees of rotational freedom relative to the other capture member. An external fixation system including fixation components according to this invention allows movement of the bone along six separate axes, a combination of three orthogonal translational axes and three orthogonal rotational axes.

In one embodiment according to this invention, a fixation component having a unique joint allows simultaneous locking of one capture member and the joint. In addition, one capture member may be locked in place while the second capture member continues to freely rotate. In this manner, the surgeon is able to lock one capture member and continue to rotate the second capture member for final positioning. The surgeon is also able to loosen only one capture member to gain additional reduction, if required, without losing placement, as occurs with current systems when additional reduction is required.

Consider one example of systems and devices according to this invention. As shown in FIGS. 1–6, a bar-to-pin fixation component 20 includes first capture member 24 and second capture member 22. First capture member 24 retains pin 26, while second capture member 22 is configured to retain bar 28, as shown in FIG. 3. The base 30 of first capture member 24 includes a groove 32, while the head 34 of first capture member 24 contains a wedge 36, which together are adapted to retain pin 26. Likewise, a base 38 and a head 40 of second capture member 22 include a groove 42 and a wedge 44, together adapted to retain bar 28. In one embodiment, groove 42 of second capture member 22 has splines 46, which provide rotational stability of bar 28 and penetrate the surface of bar 28 when second capture member 22 is tightened. Alternatively, the second capture member may be adapted to retain a pin and the first capture member may be adapted to retain a bar. In an alternative embodiment, both the first and second capture members are configured to retain a bar. In another embodiment, one capture member is adapted to retain a wire, while the other capture member is adapted to retain a bar.

Figure 2:
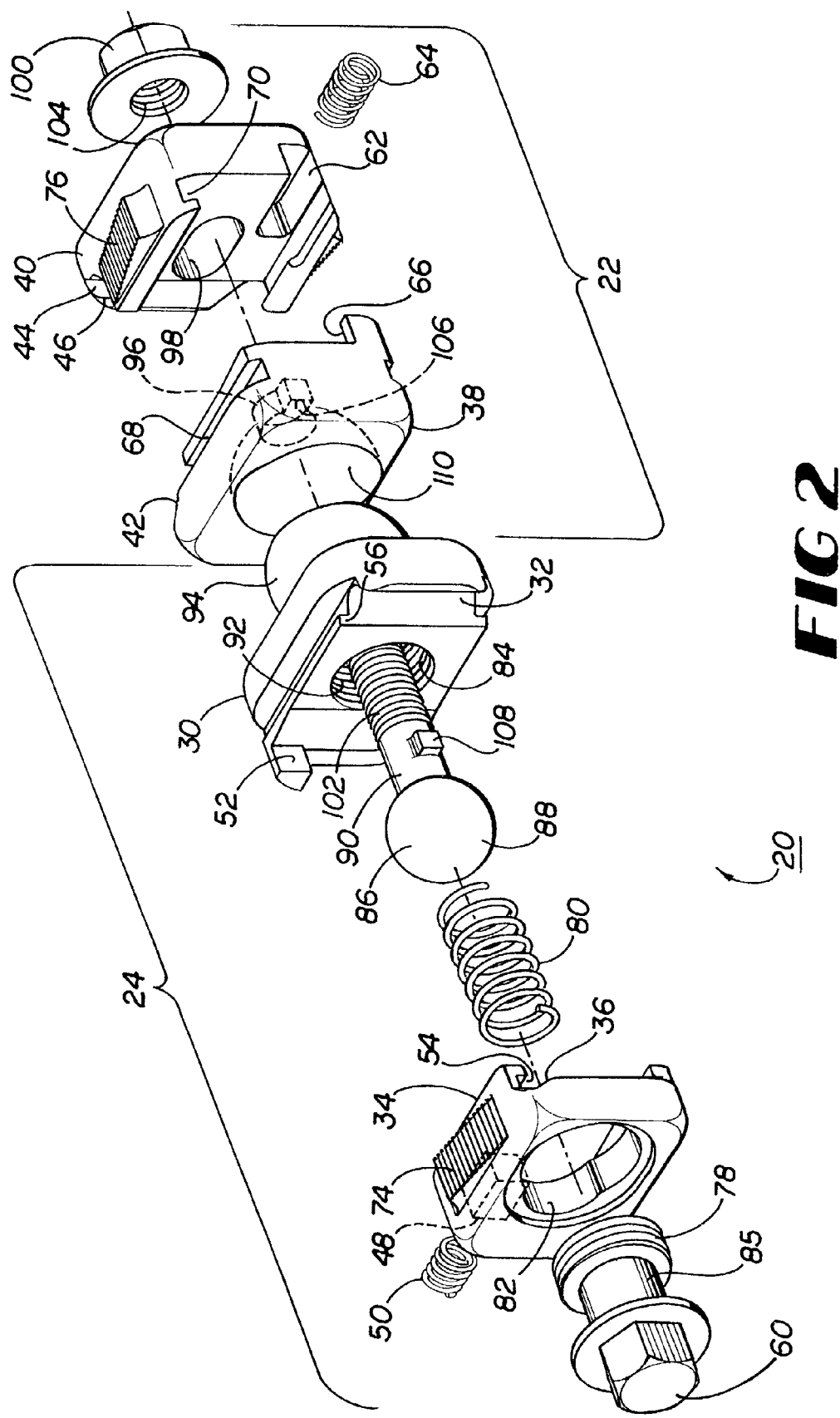
FIG. 2 is an exploded perspective view of the fixation component of FIG. 1.
Figure 3:
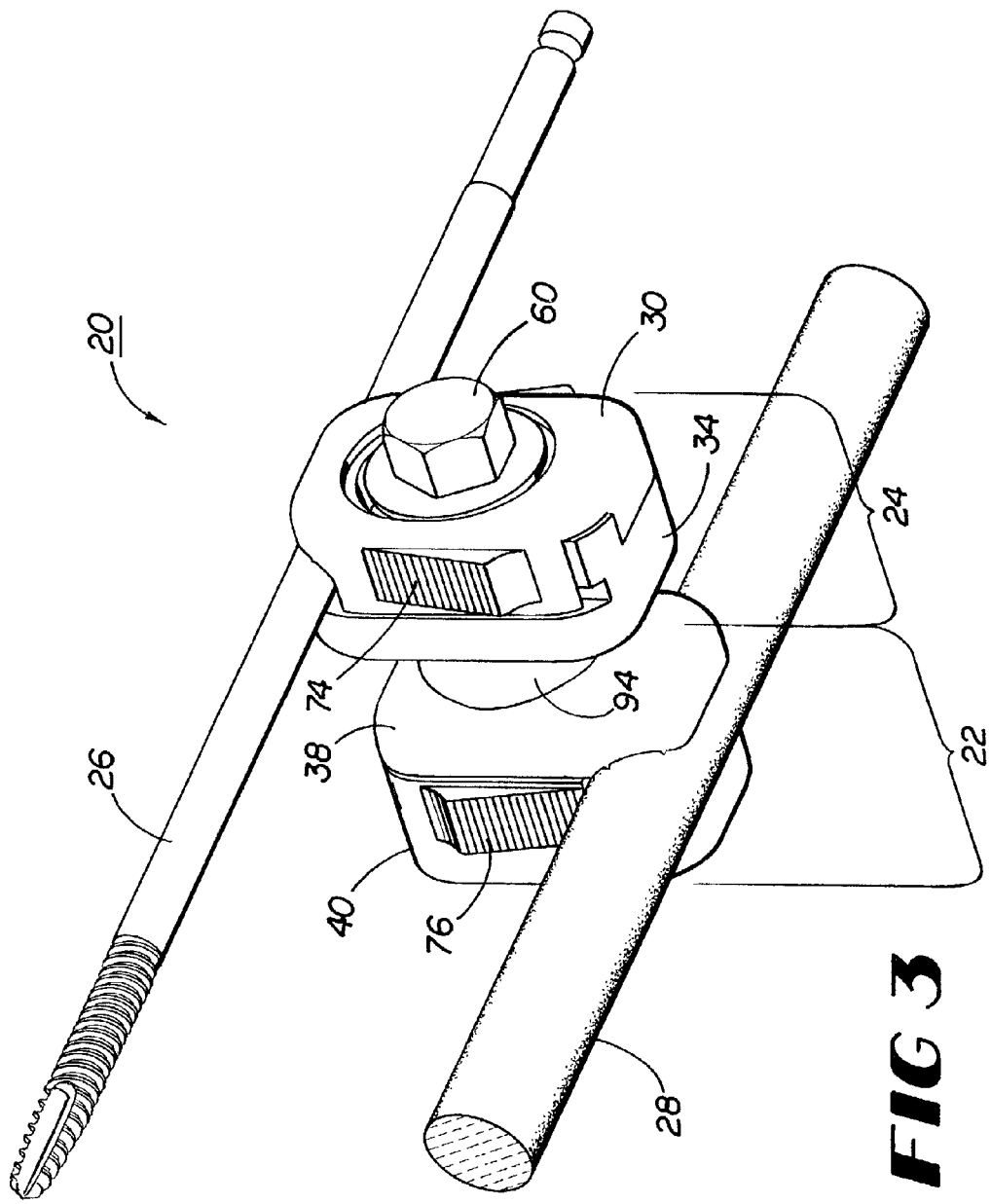
FIG. 3 is a perspective view of the fixation component of FIG. 1 with a pin and bar inserted.
Figure 4:
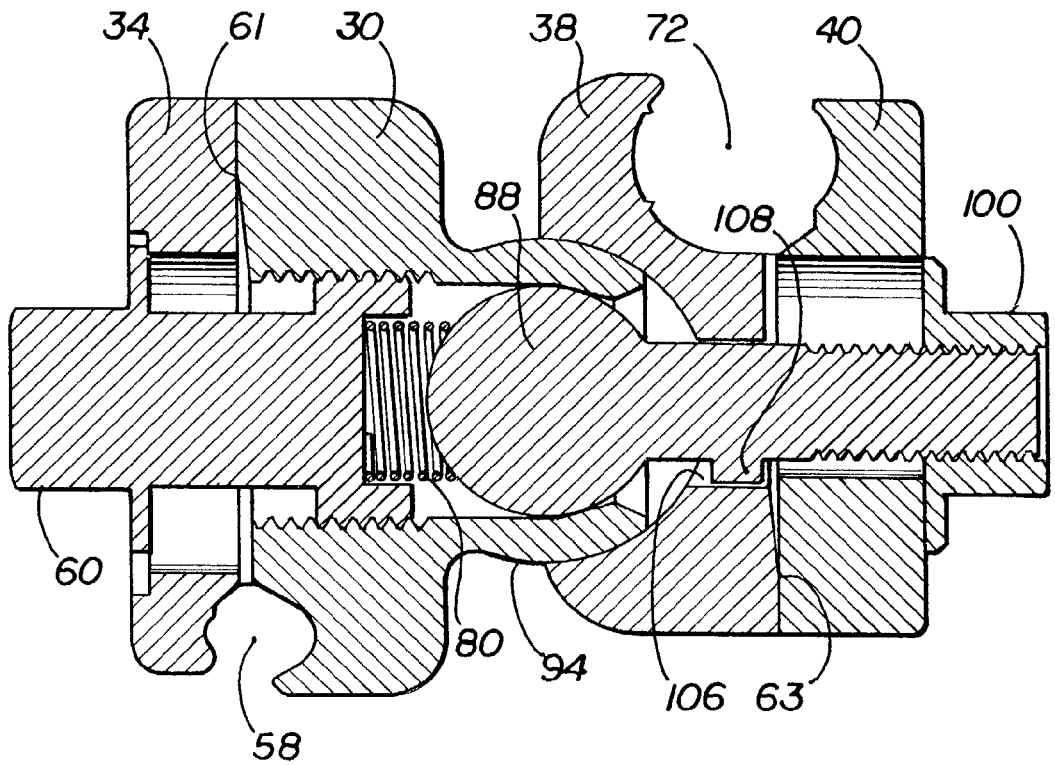
FIG. 4 is a cross-sectional view of the fixation component taken along lines 4—4 in FIG. 1.
Figure 5:
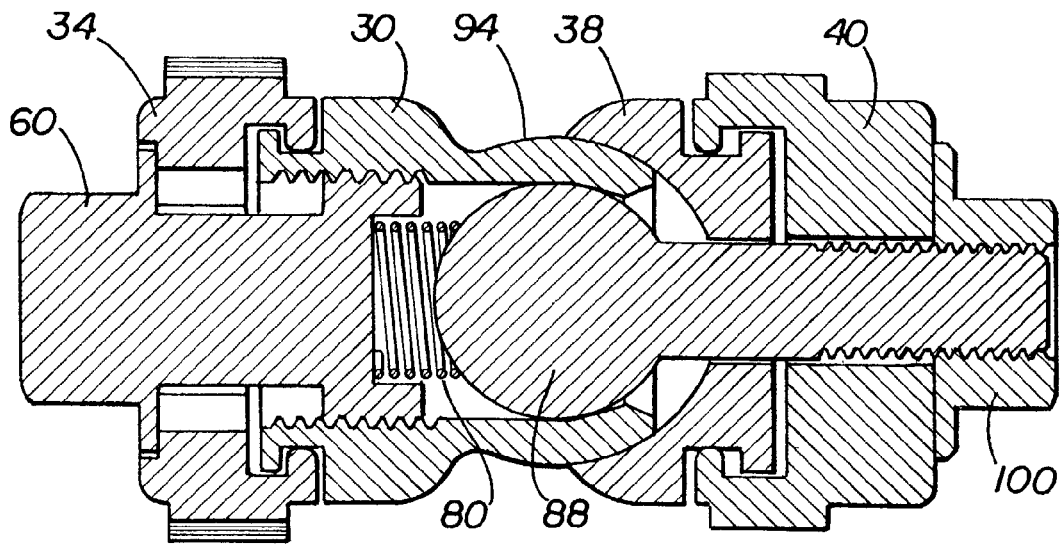
FIG. 5 is a cross-sectional view of the fixation component taken along lines 5—5 in FIG. 1.
Figure 6:
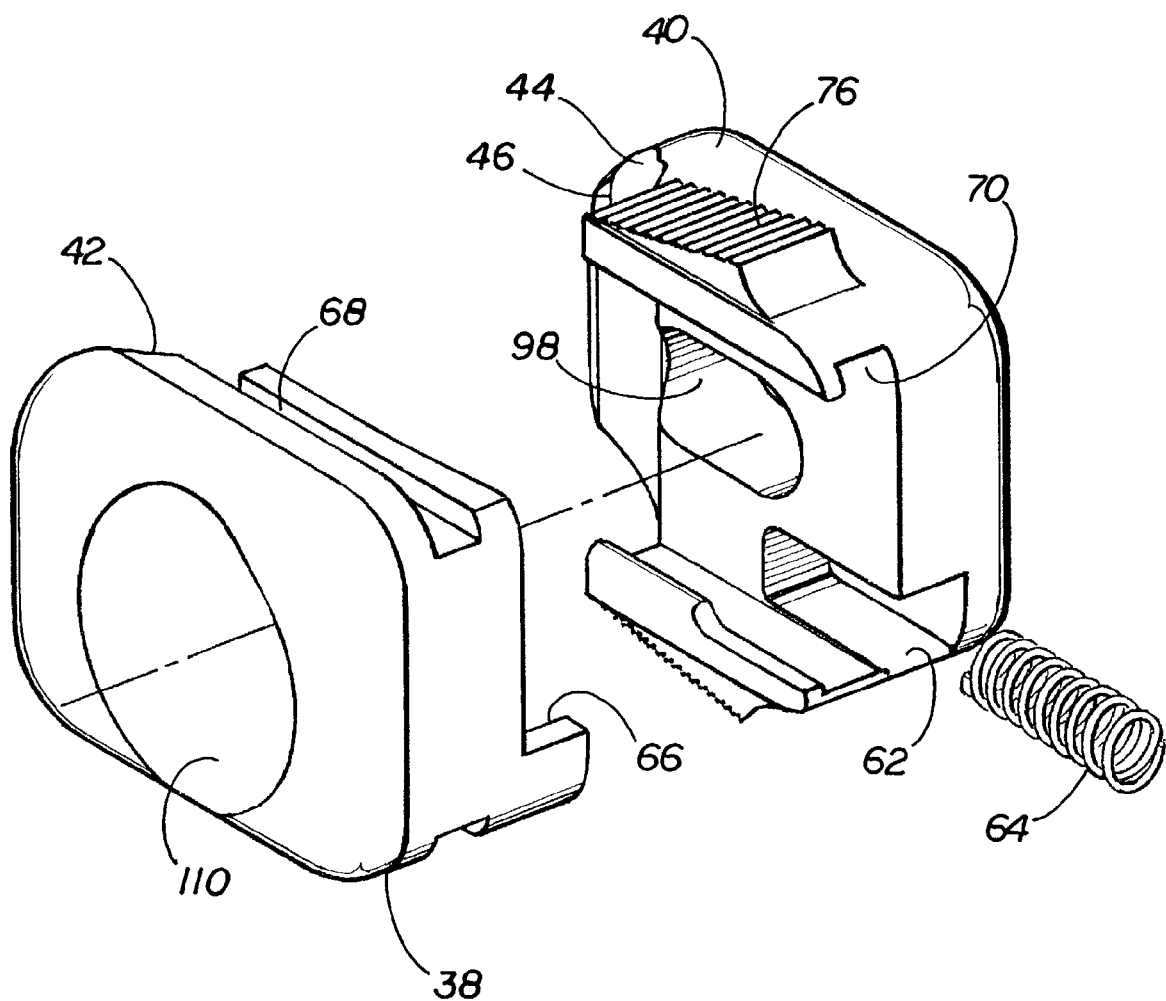
FIG. 6 is an exploded perspective view of the second capture member of FIG. 1.

As shown in FIG. 2, head 34 of first capture member 24 has a recess 48 adapted to receive a spring 50, while base 30 of first capture member 24 includes a stop 52. A first track 54 on each side of head 34 slides in a second track 56 on each side of base 30, allowing head 34 and base 30 of first capture member 24 to translate with respect to each other. In an alternative embodiment, second track 56 slides in first track 54. In one embodiment, one of first and second tracks 54, 56 is an L-shaped track, while the other track is shaped to receive the L-shaped track. As a force in a direction perpendicular to the pin is exerted against groove 32 and wedge 36 of first capture member 24, head 34 moves, compressing spring 50 against the extended portion of base 30. Spring 50 compresses until it exerts a force in a direction perpendicular to pin 26 that is equal and opposite to the force exerted against wedge 36. At that point, head 34 stops moving and holds pin 26 in groove 32 and wedge 36, which together form channel 58. After pin 26 is located in channel 58, the force of spring 50 will temporarily hold the pin in position until the angular position of channel 58 is set by tightening a first fastener 60. Base 30 of first capture member 24 includes an elevated portion 61, as shown in FIG. 4, forcing two points of contact between base 30 and head 34 in order to increase the holding power of first capture member 24. Base 38 of second capture member 22 also includes an elevated portion 63, also shown in FIG. 4, which increases the holding power of second capture member 22 in the same manner.

Second capture member 22 includes also includes a cartridge mechanism for retaining bar 28. Head 40 of second capture member 22 has a recess 62 adapted to receive a spring 64, while base 38 of second capture member 22 includes a stop 66. A first track 68 on each side of head 40 slides in a second track 70 on each side of base 38. In an alternative embodiment, second track 70 slides in first track 68. In one embodiment, one of first and second tracks 68, 70 is an L-shaped track, while the other track is shaped to receive the L-shaped track. Groove 42 and wedge 44 of second capture member form second capture member channel 72, which receives bar 28. Bar 28 is retained in second capture member 22 in the same manner as first capture member 24 retains pin 26.

In an alternative embodiment, one or both capture members may include two recesses for receiving two springs and two spring stops. In the embodiments shown, the recess, spring, and stop are located on one side of the capture member. In an alternative embodiment, the recess, spring, and stop are in the middle of the capture member, or are on the other side of the capture member. In one embodiment, heads 40 and 34 of capture members 22 and 24, respectively, includes grip surfaces 74 and 76 for gripping and sliding heads 40 and 34 in relation to bases 38 and 30, respectively. In one embodiment, grip surfaces 74 and 76 include ridges.

A threaded end 78 of first fastener 60 is adjacent a biasing element, such as center spring 80, and passes through a keyhole aperture 82 in head 34 of first capture member 24, mating to internal threads 84 in base 30 of first capture member 24. Keyhole aperture 82 of head 34 of first capture member 24 allows a reduced diameter neck 85 of first fastener 60 to translate within aperture 82. Tightening of first fastener 60 locks first capture member 24 and rigidly retains pin 26. In an alternative embodiment, aperture 82 is circular, or any other suitable shape.

A connector 86 having an end 88 and a shaft 90 extends through a keyhole aperture 92 in base 30 of first capture member 24. In one embodiment, connector 86 is a ball stud, as shown in FIG. 2, having a spherical end. End 88 of connector 86 is received in a planetary member 94 of base 30 of first capture member 24. As used herein, a planetary member refers to an object that is received in another object, and that receives another object within itself. In one embodiment, planetary member 94 is an outer sphere, as shown in the figures. Shaft 90 of connector 86 extends through an aperture 96 in base 38 of second capture member 22 and an aperture 98 of head 40 of second capture member 22, and mates with a second fastener 100. Threads 102 on shaft 90 of connector 86 mate with internal threads 104 of second fastener 100.

A slot 106 in aperture 96 of base 38 of second capture member 22 is adapted to receive a key 108 on shaft 90 of connector 86. Key 108 and slot 106 thus prevent rotation of connector 86 within second capture member 22. In another embodiment, any suitable mechanism for preventing rotation of the connector is used. In other words, the connector fits through the base of the first capture member and the end is received in the planetary member of the base, while the shaft of the connector extends through both the base and head of the second capture member and threads to a second fastener. A planetary member, for example outer sphere 94, fits within a cooperating surface 110, which is machined into the one side of base 38 of second capture member 22. Tightening of second fastener 100 on second capture member 22 draws connector 86 into planetary member 94, locking the second capture member and the joint to make it rigid. In one embodiment, one or both of the planetary member and cooperating surface may be tapered. For example, a taper of 10°, 15°, 20° or 30° may be used on each.

The joint mechanism described above allows the second capture member to rotate with respect to the planetary member of the first capture member, and allows the first capture member to grasp and lock a pin while permitting the second capture member to continue to rotate. Independent tightening of the capture members provides the surgeon flexibility to snap a fixation element to a capture member and then to manipulate the second capture member before locking the second capture member in order to achieve a more stable frame. In this manner, independent tightening of each capture member of the external fixation component allows more precise angular positioning.

Other embodiments, such as a bar-to-bar fixation component, and a bar-to-wire fixation component, also may contribute to a more stable, more adjustable external fixation system. These embodiments function similarly to the bar-to-pin fixation component, with the capture members having a wedge and groove adapted to form a channel sized for receiving either a bar or a wire, depending on the component.

In one embodiment, a cartridge locking of the pin and bar is provided, as described above. However, in alternative embodiments, other one-piece designs may be used. For example, a solid piece of aluminum metal having the shape of the two part head and base cartridge construct of the two capture members may be used. This one-piece design includes a channel in each one piece capture member and a slot that extends close to the rear portion of the capture member. The slot causes the material to behave similar to a spring and allows the capture member to open when pressure is placed against it, so that a fixation element may be snapped into place in the channel.

In an alternative embodiment, a fixation component is designed for attachment to a circumferential external fixator system, such as an ILIZAROV® brand system, a SPATIAL FRAME® brand system, or other spatial frame, to achieve a hybrid external construct. In this embodiment, the fixation component includes a capture member for retaining a bar and a capture member for retaining a half or circumferential ring having a generally rectangular cross-section. Use of a fixation component having a capture member for retaining a ring allows a surgeon to create a hybrid frame, using both a standard external fixation system and a system that includes a circumferential external frame. This hybrid system is very useful in adapting a system for treating a shaft fracture, or typical in-line fracture, to one for treating a plateau fracture, which is a fracture in a joint space.

One embodiment of a fixation component of this invention is made from titanium and aluminum. In this embodiment, the heads of the capture members are made from aluminum and the remaining parts from titanium. In alternative embodiments, fixation components are made from metals, alloys, plastics, composites, ceramics, or any other suitable material.

For a further discussion of fixation components, including various other and alternative embodiments of fixation components according to this invention, the reader is referred to commonly-assigned U.S. application Ser. No. 10/067,052, which has previously been incorporated herein by reference in its entirety.

Figure 7:
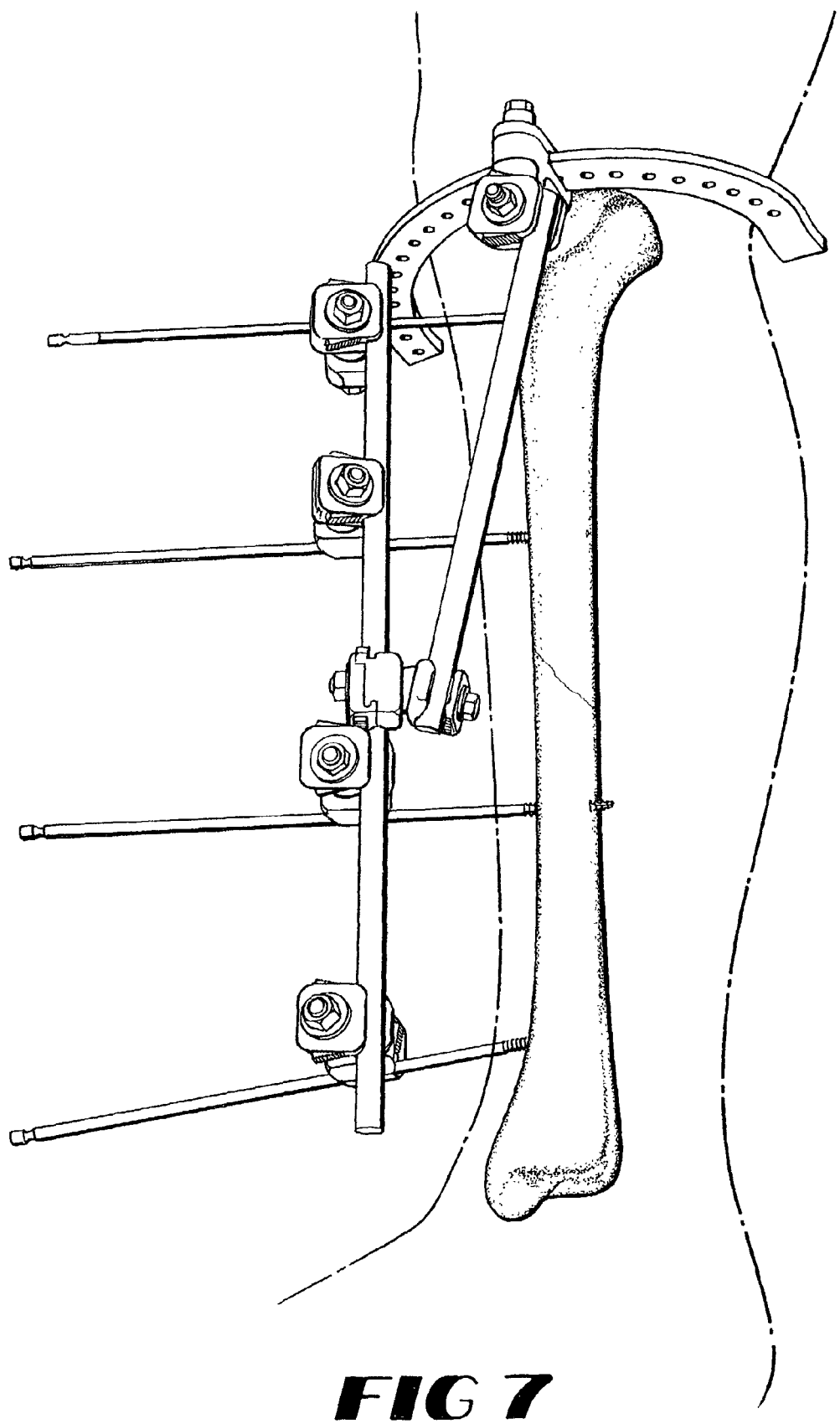
FIG. 7 is a perspective view of an external fixation system according to one embodiment of this invention.
Figure 8:
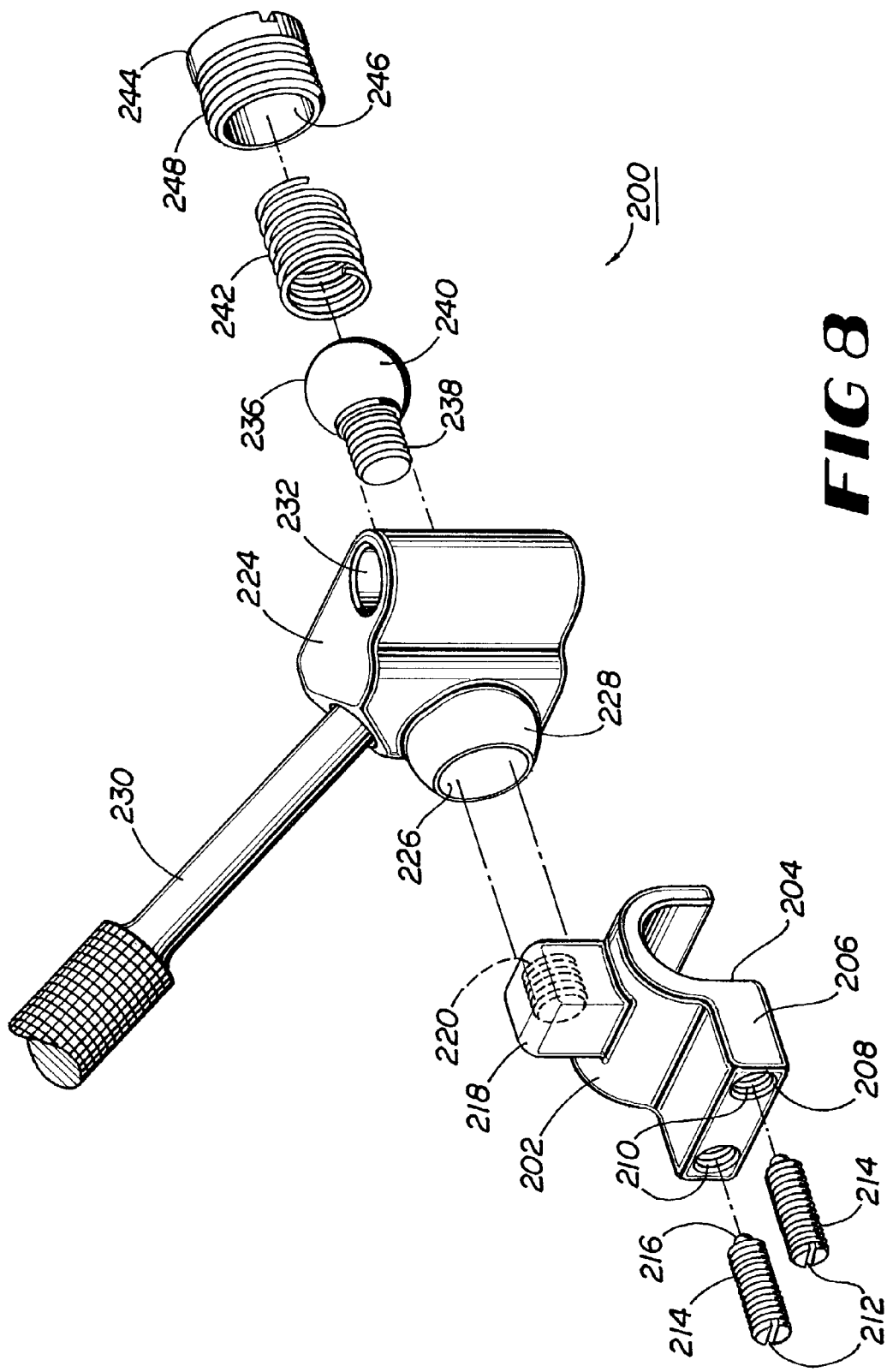
FIG. 8 is an exploded view of a drill guide according to one embodiment of this invention.

One method of using one form of structure according to this invention, shown in FIG. 7, is as follows:

At least two half pins are self-drilled into a bone, one on either side of a bone fracture. One bar-to-pin fixation component is connected to each pin by placing each pin into the capture member of each fixation component sized to receive a pin, such as the first capture member of the bar-to-pin fixation component shown in FIG. 1. Each fixation element is placed into the fixation component from the side for easy placement. After a pin is in place, the first fastener is tightened, so that the pin is retained in the capture member, while the second capture member and joint continue to freely rotate. Bars are then snapped into the bar capture member of the fixation components, forming a frame for the system. As each bar is added, the fixation components are adjusted as required by loosening the joint and second capture member, so that optimal positioning may be obtained. Bar-to-bar fixation components and bar-to-pin fixation components may be added to expand and connect the frame as required. If it is necessary or desirable to utilize a circumferential ring or half ring with a system for complex fractures, as shown in FIG. 7, additional fixation components having capture members designed to retain the rectangular bar of a ring are used to join the standard system to the specialized frame. A T-component is used to capture the rectangular bar of a ring and link it to a bar of the original frame, forming a hybrid system. If additional reduction is required, one capture member of any component may be loosened without losing placement of the system. A T-component may also be used to provide stability to an existing system that has already been placed using standard fixation component designs. A plurality of clamps may be used in various configurations to achieve stability for different fractures.

Similar instrumentation and devices may be used in other areas, such as to provide a fixed reference to a pin. Constructs made under the present invention are stable and provide for a wide variety or placements. Embodiments of an external fixation component according to this invention may also be adapted for use with an image guided surgery system to provide stability to a reference frame or other guidance target or mechanism.

As noted above, methods, systems, and devices according to this invention also provide drill guides for optimal placement of fixation elements into a patient's bone, particularly the placement and positioning of pins. After placement of the first two pins, for example, as described above in conjunction with FIG. 7, one pin is typically above the fracture and the second pin is typically below the fracture. Each pin is attached to a bar using a fixation components.

Often, it is desirable for stability and other reasons to place more than two pins into the patient's bone as part of an external fixation system. To place a third and any subsequent pins, the surgeon, in the past, was required to attach the fixation component to the bar and drill through the appropriate channel or passageway in the fixation component to insert the pin. If the surgeon placed the pin prior to attaching and positioning the fixation component on the bar, it would most likely result in having to reinsert or redrill the pin once the surgeon tried to couple the pin to the bar using a fixation component. Drill guides according to the present invention provide an easier and more effective way of inserting third and subsequent pins into a patient's bone, while allowing for increased freedom so that the surgeon may place the pin in the most optimal position knowing that the fixation component will attach the pin to the bar as desired.

One embodiment of a drill guide according to this invention includes a collar frame and a guide frame connected by a joint. The collar frame includes a collar adapted to receive a bar of an external fixation system. The guide frame includes a bore through which a fixation element, such as a pin, may be inserted for placement into a patient's skin and bone. A drill, drill bit, depth gauge, or tissue sleeve may also be inserted through the bore of the guide frame. The collar frame and guide frame are connected by a joint, such as a ball joint or a pivot, that allows the collar and guide frames to rotate with respect to each other. In one embodiment, the joint may allow rotation of up to 50° in any plane (25° each way), increasing the degree of freedom of rotation. In another embodiment more angulation may be provided. Thus, the collar frame is provided three axes of rotation relative to the guide frame (e.g., typical "x," "y," and "z" axes) and vice versa. In another embodiment, relative rotation may be provided in only one axis or two axes.

Figure 9:
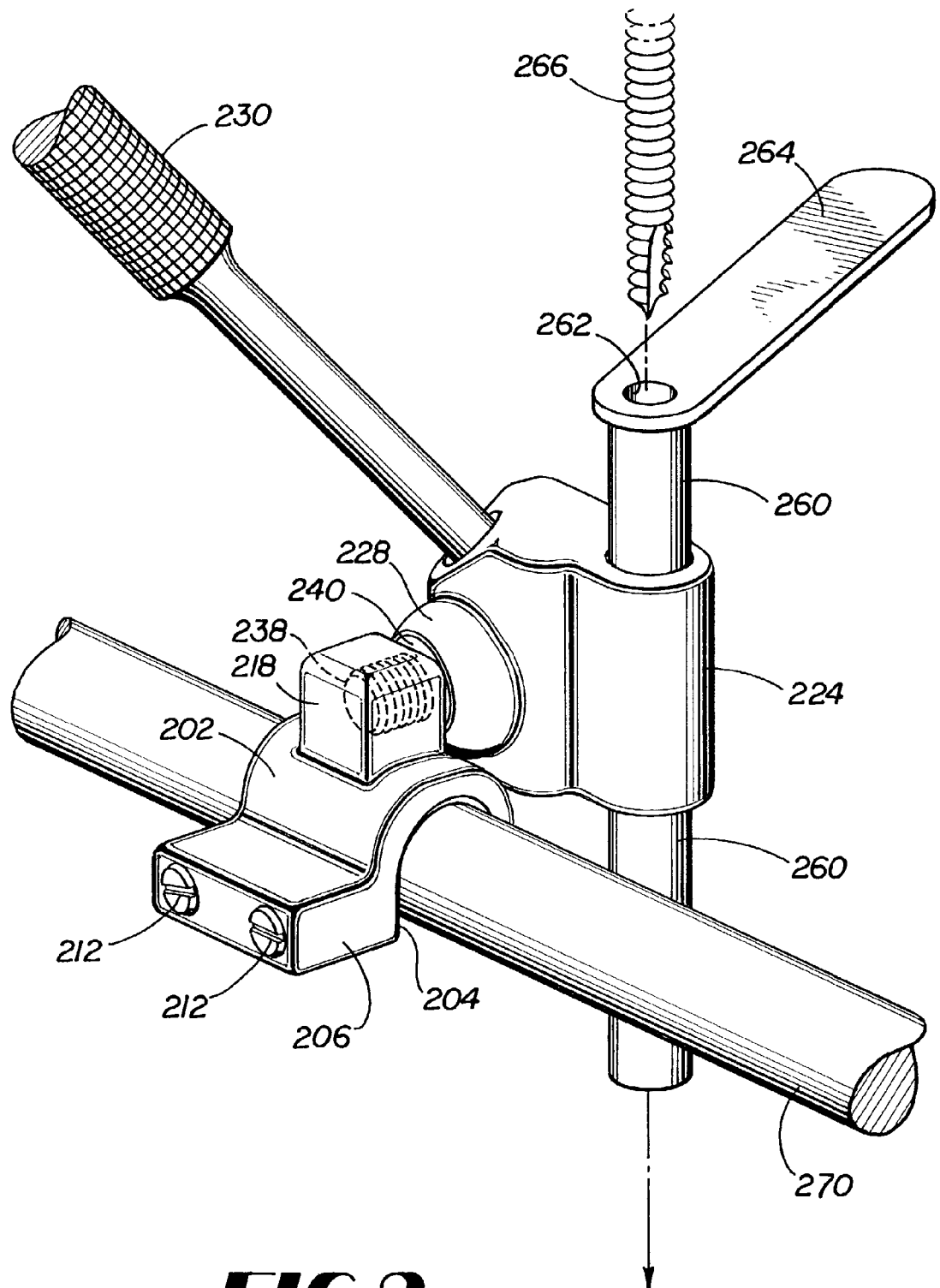
FIG. 9 is a perspective view of the drill guide of FIG. 8 placed on a bar, with a tissue sleeve inserted, and a pin.
Figure 10:
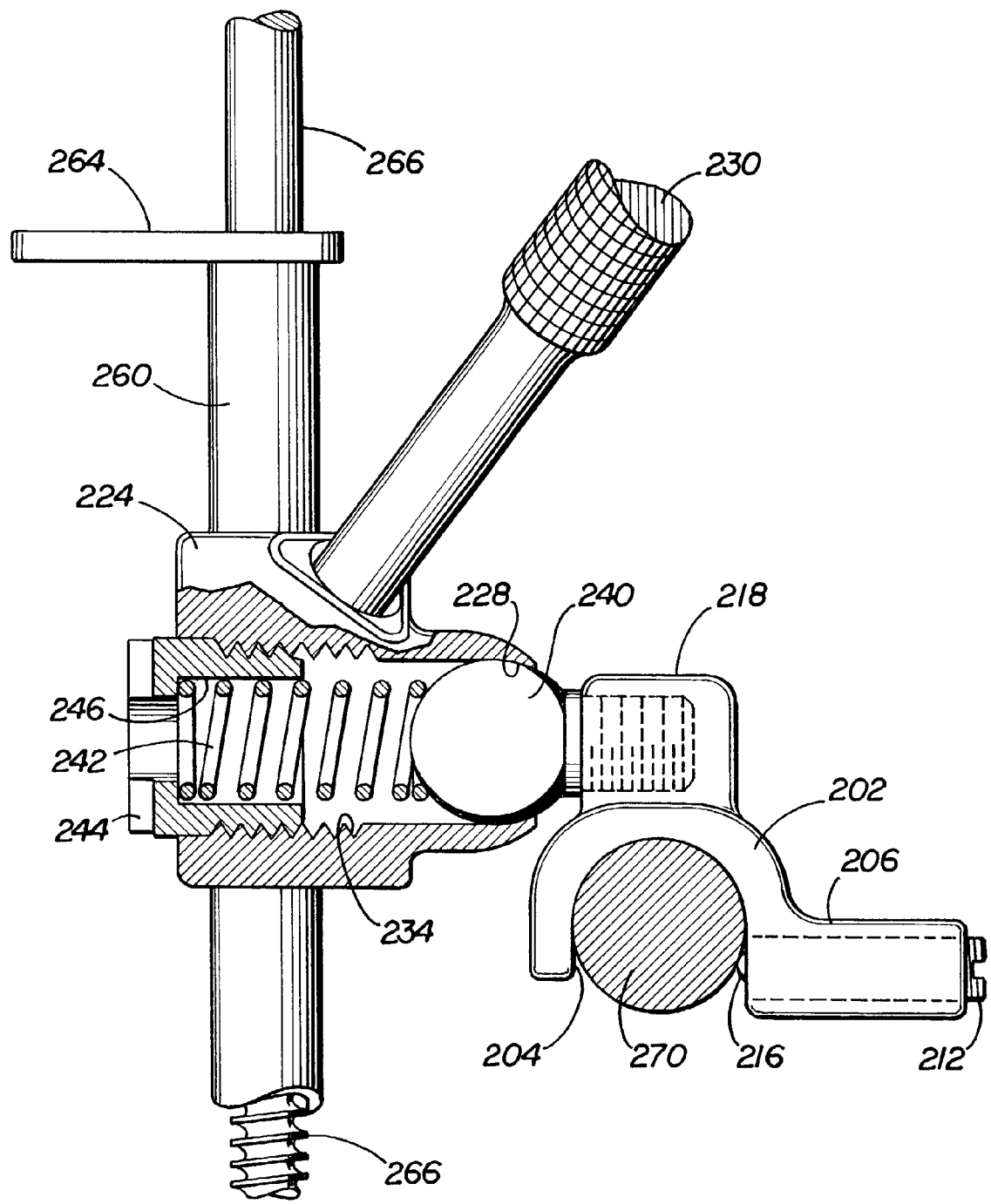
FIG. 10 is a cross-sectional view of the drill guide of FIG. 8 placed on a bar and with a tissue sleeve and pin inserted.

Referring now to FIGS. 8–11, according to one embodiment, a drill guide 200 includes a collar frame 202 and a guide frame 224. Collar frame 202 includes a collar 204 within which a bar 270 of an external fixation system may fit. At one end of collar 204, an extension 206 extends from collar 204 and away from guide frame 224. Extension 206 includes two bores 208 that receive ball plungers 212. Bores 208 have internal threads 210 adapted to receive threads 214 of ball plungers 212. As shown in FIG. 10, tips 216 of ball plungers 212 protrude out of bores 208, allowing collar 204 to snap fit to bar 270. The fit of bar 270 within collar 204 is such that drill guide 200 may easily move linearly along or rotate about bar 270. For the embodiment shown in FIGS. 8–11, collar frame 202 preferably has the same or approximate width as a second capture member 278 of a fixation component 272, shown in FIG. 11, to minimize the risk of an improper fit between such a fixation component that is later used to couple an inserted pin to the bar.

A portion 218 of collar frame 202 includes a recess 220 with internal threads 222 that are adapted to receive a threaded shaft 238 of a connector 236. Connector 236 is inserted through an aperture 226 in guide frame 224. Threaded shaft 238 extends completely out of guide frame 224 and mates with internal threads 222 to secure collar frame 202 to guide frame 224. A retainer ball 240 of connector 236 is situated within an outer sphere 228 of guide frame 224 allowing guide frame 224 to rotate with respect to collar frame 202 and vice versa. Outer sphere 228 is dimensioned to limit travel of retainer ball 240 to a predetermined angle. One embodiment allows rotation of up to 50° in any plane (25° each way). In the embodiment shown in FIGS. 8–11 for use in an external fixation system with fixation components according to the embodiments shown in FIGS. 1–7, the rotational relationship between guide frame 224 and collar frame 202 is designed to approximate or mimic the rotational relationship between a first capture member 274 and a second capture member 278 of a fixation component 272, respectively.

Inserted into guide frame 224 adjacent to retainer ball 240 is a biasing element, such as spring 242. Spring 242 provides tension, allowing ball retainer 240 to rotate within guide frame 224 as desired. A fastener 244 secures spring 242 within guide frame 224. Threads 248 mate with internal threads 234 of guide frame 224, as shown in FIG. 10. Fastener 244 may have a recess 246 such that a portion of spring 242 is within recess 246 once fastener 244 is attached to guide frame 224, as shown in FIG. 10. Tightening of fastener 244 adjusts the tension in spring 242, thereby affecting the rotation of ball retainer 242.

Guide frame 224 also includes a handle 230. Handle 230 extends from guide frame 224 and may be used to move drill guide 200 linearly or rotationally along a bar of an external fixation system. In one embodiment, handle 230 may inserted into guide frame 224, welded, and belt smoothed. Other manners of securing handle 230 to or within guide frame 224 are well known to those skilled in the art. In an alternative embodiment, drill guide 200 may not include a handle. Guide frame 224 may be stabilized by any functional structure, including a tissue sleeve 260, as described below, or a fixation element, drill bit, or other device inserted through drill guide 200.

Figure 11:
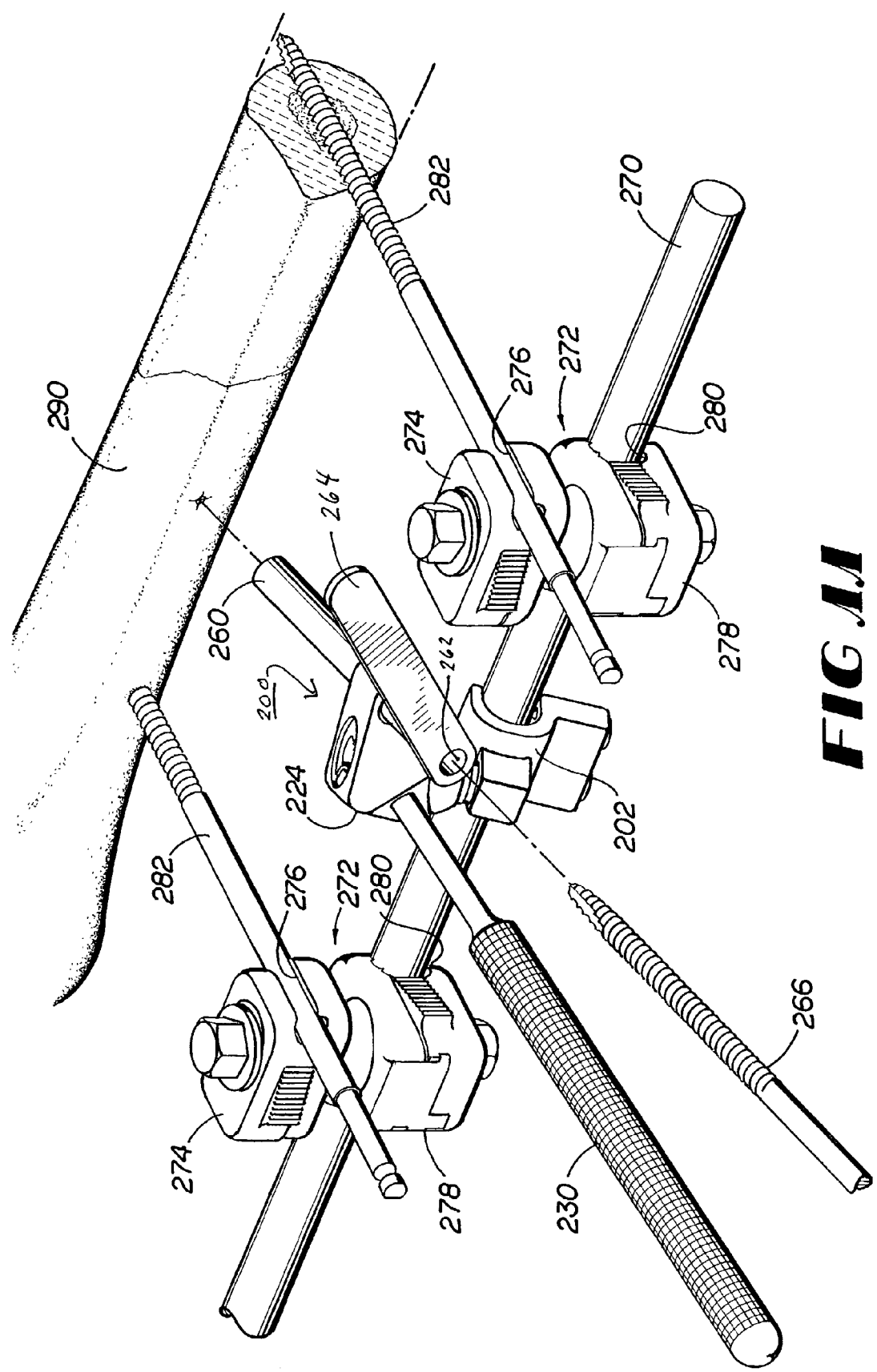
FIG. 11 is a perspective view of the drill guide of FIG. 8 placed on an external fixation system.

A bore 232 is provided in guide frame 224 for receiving a fixation element, such as a pin or wire, and/or a tissue sleeve 260, as shown in FIGS. 9–11. Bore 232 may also receive a drill, drill bit, or depth gauge. Tissue sleeve 260 may assist in pushing soft tissue away from the end of a fixation element as the fixation element is being inserted into the patient's body and placed into the bone. Tissue sleeve 260 includes a channel 262 through which a fixation element, such as a pin or wire, may be inserted. Tissue sleeve 260 also includes a handle 264 for moving tissue sleeve 260 axially or rotationally within bore 232. In an alternative embodiment, a tissue sleeve or drill sleeve may be integrally formed in drill guide 200. For the embodiment shown in FIGS. 8–11, the position of bore 232 relative to collar 204 and bar 270 is approximately the same as the position of channel 276 of first capture member 274 relative to channel 280 of second capture member 278 and bar 270. Accordingly, when a pin is inserted through bore 232 of drill guide 200 and into a patient's bone and drill guide 200 is removed from bar 270, the positioning of the pin is engineered to be compatible with a fixation component that is later used to couple the pin to bar 270. In one embodiment, collar frame 202 and guide frame 224 may be machined from stainless steel and color-coded to the bars, pins, and other parts of an external fixation system with which drill guide 200 is designed to be used.

Drill guides according to the invention allow for placement of a pin before the corresponding fixation component is placed onto the bar, resulting in such pin placement being unconstrained by a fixation component. Prior systems are limited because third and subsequent pins must be placed according to a prior location or position of fixation components (i.e., prior systems resulted in the surgeon drilling through the fixation component, thereby limiting possible positioning of the pin). The added flexibility provided by drill guides according to this invention is even more critical when pins or other fixation elements are being placed in an area of vascular and nerve structures.

Referring now to FIG. 11, according to one method for using an embodiment of a drill guide according to the invention, two half pins 282 are self-drilled into a bone 290 of a patient, one on either side of a bone fracture. One bar-to-pin fixation component 272 is connected to each pin 282 by placing each pin 282 into the capture member of each fixation component sized to receive pin 282, such as first capture member 274 of fixation component 272 shown in FIG. 11. Pins 282 are placed into fixation components 272 from the side for easy placement. After pins 282 are in place, fasteners are tightened, so that pins 282 are retained in their respective first capture members 274, while second capture members 278 of fixation components 272 continue to freely rotate. Bar 270 is then snapped into second capture members 278 of fixation components 272.

If additional pins are desired, collar 204 (FIG. 10) of drill guide 200 is slipped onto bar 270. Ball plungers 212 (FIG.

10) allow for a snap contained fit while still allowing linear and rotational motion of drill guide 200 along bar 270. Drill guide is moved axially along bar 270 and/or rotated to the desired position to place a pin 266 into the bone 290 of a patient. If desired, tissue sleeve or drill sleeve 260 may be inserted into bore 232 (FIG. 8) of drill guide 200 for drilling of pin 266, or pre-drilling such as a pilot hole. Tissue sleeve 260 includes a handle 264 and a channel 262 through which pin 266 may be inserted. After the desired position is identified, a stab incision is made into the skin and pin 266 is placed through tissue sleeve 260 (or just bore 232, if no tissue sleeve is used), which is in bore 232, and into bone 290. Drill guide 200 is removed and a fixation component is used to couple pin 266 to bar 270.

For simplicity, the fixation components shown in FIG. 11 are embodiments of fixation components according to this invention that are described above and shown in FIGS. 1–7. However, it should be understood that drill guides according to the present invention may be for use with any number of fixation components, as well as any number of fixation elements and external fixation systems. Accordingly, drill guides according to the invention are not limited to embodiments of drill guides for use with embodiments of fixation components according to the invention.

Figure 12:
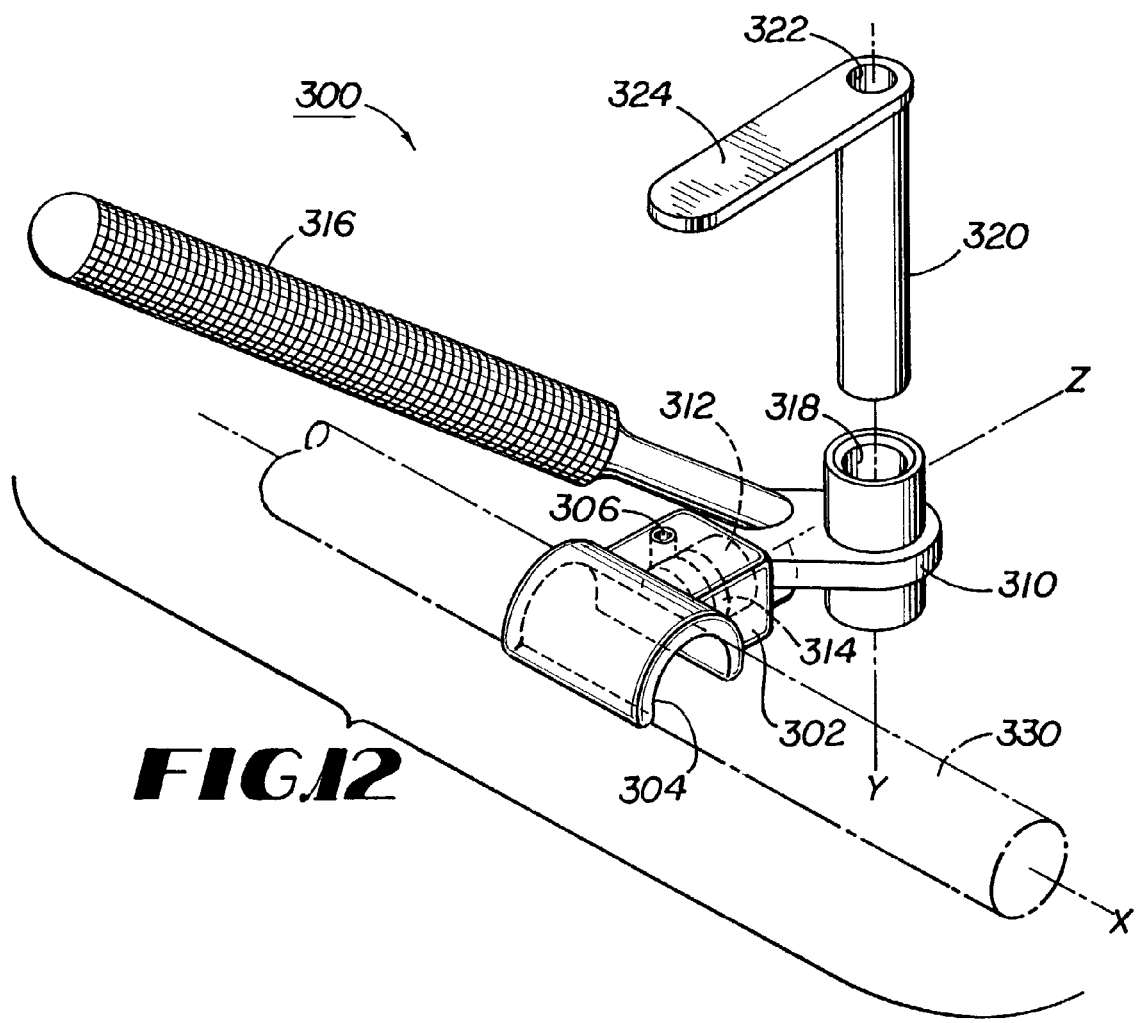
FIG. 12 is a perspective view of a drill guide according to an alternative embodiment of the invention placed on a bar and with a tissue sleeve shown.
Figure 13:
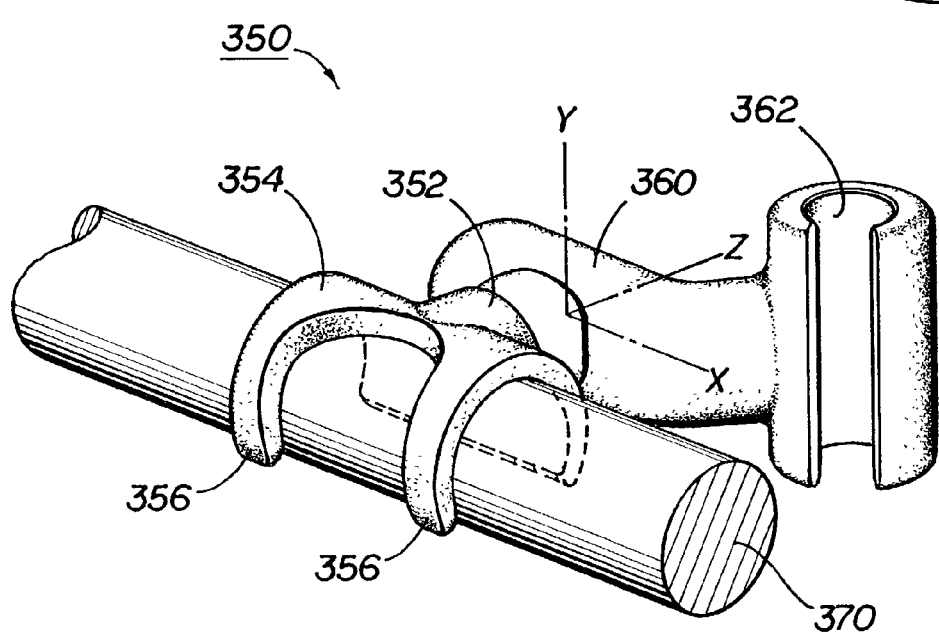
FIG. 13 is a perspective view of a drill guide according to an alternative embodiment of the invention placed on a bar.

Alternative embodiments of drill guides according to this invention are shown in FIGS. 12 and 13. As shown in FIG. 12, according to one embodiment, a drill guide 300 includes a collar frame 302 and a guide frame 310. Collar frame 302 includes a collar 304 within which a bar 330 of an external fixation system may fit. Collar 304 does not clip or snap fit to bar 330, but rather collar 304 slides and rotates freely (approximately 180 degrees or less) about bar 330. A counterbore (not shown) in collar frame 302 telescopically receives a projecting stud 312 from guide frame 310. Stud 312 includes an annular recess or groove 314 that accommodates and is in tangential contact with a retaining pin 306 in collar frame 302, allowing for relative rotation between collar frame 302 and guide frame 310 along the z-axis.

Guide frame 310 also includes a handle 316. Handle 316 extends from guide frame 310 and may be used to move drill guide 300 axially or rotationally along a bar of an external fixation system, such as bar 330. Handle 316 may be inserted into guide frame 310, welded, and belt smoothed. Other manners of securing handle 316 to or within guide frame 310 are well known to those skilled in the art. Alternatively, drill guide 300 may not include a handle or a stabilizing means other than a handle, such as those discussed above in conjunction with the exemplary embodiment shown in FIGS. 8–11, may be used.

A bore 318 is provided in guide frame 310 for receiving a fixation element, such as a pin or wire, and/or a tissue or drill sleeve, such as tissue sleeve 320, as shown in FIG. 12. Bore 318 may also receive a drill, drill bit, or depth gauge. Tissue sleeve 320 includes a channel 322 through which a fixation element may be inserted. Tissue sleeve 320 also includes a handle 324 for moving tissue sleeve 320 axially or rotationally within bore 318 of drill guide 300. In an alternative embodiment, a tissue sleeve or drill sleeve may be integrally formed in drill guide 300.

Another embodiment of a drill guide according to this invention is shown in FIG. 13. As shown in FIG. 13, a drill guide 350 includes a collar frame 352 that is made of a high strength thermoplastic, such as Delrin® or Ultemg® polyetherimide. Collar frame 352 includes a collar 354 with bifurcated legs 356 that engage greater than 180 degrees of a bar 370, allowing collar 354 to clip onto bar 370. Collar 354 may be moved axially or rotationally along bar 370. Collar frame 352 is coupled to a guide frame 360 that includes a bore 362 through which a fixation element, tissue sleeve, drill, drill bit, or depth gauge may be inserted.

Optionally, collar frame 352 may be coupled to guide frame 360 by a ball joint similar to the ball joint between the collar frame and the guide frame of the embodiment described and shown in FIGS. 8–11. Alternatively, collar frame 352 may be coupled to guide frame 360 by a joint similar to the joint between the collar frame and the guide frame of the embodiment described and shown in FIG. 12.

In another embodiment, a drill guide according to the invention may be used in the spinal area for drilling pedicle screws into the pedicle with the drill guide aligning onto the spinal rod.

The foregoing description of certain exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and certain exemplary embodiments described therein.

What is claimed is:

1. A drill guide comprising:
   a collar frame with a collar dimensioned to receive a portion of an orthopedic fixation system;
   a guide frame including a bore through which a fixation element of the orthopedic fixation system may be inserted, the guide frame coupled to the collar frame such that the coupling allows the guide frame and the collar frame to rotate about at least one axis relative to each other;
   a connector with a threaded end and a ball end;
   a recess of the collar frame with internal threads adapted to receive the threaded end of the connector;
   an outer cavity of the guide frame adapted to receive the ball end of the connector;
   a fastener with a recess and a threaded end adapted to mate with internal threads in an aperture of the guide frame; and
   a biasing element adjacent the ball end of the connector and wherein the recess of the fastener may receive a portion of the biasing element.

2. The drill guide of claim 1, wherein the collar is dimensioned to move linearly, rotationally, or linearly and rotationally about the portion of the orthopedic fixation system.

3. The drill guide of claim 1, wherein the portion of the orthopedic fixation system is a bar.

4. The drill guide of claim 1, wherein the fixation element is a half pin.

5. The drill guide of claim 1, further comprising a tissue sleeve integrally formed in the guide frame.

6. The drill guide of claim 1, wherein the collar frame and the guide frame rotate about three axes relative to each other.

7. The drill guide of claim 1, wherein the bore is dimensioned to receive a drill or a depth gauge.

8. The drill guide of claim 1, further comprising a handle extending from the guide frame.

9. The drill guide of claim 1, wherein the collar is adapted to receive the portion of the orthopedic fixation system from a direction generally perpendicular to the longitudinal axis of the portion of the orthopedic fixation system.

10. The drill guide of claim 1, wherein the collar defines a channel.

11. The drill guide of claim 1, wherein the bore is dimensioned to receive a tissue sleeve including a channel through which a fixation element may be inserted.

12. A drill guide comprising:
a collar frame with a collar dimensioned to receive a bar of an orthopedic fixation system;
a guide frame including a bore through which a fixation element of the orthopedic fixation system may be inserted, the guide frame coupled to the collar frame such that the collar frame and the guide frame may rotate about more than one axis relative to each other;
a connector;
a recess of the collar frame that receives a first end of the connector; and
an outer cavity of the guide frame that receives a second end of the connector,
wherein the collar frame comprises two ball plungers such that tips of the ball plungers contact a bar of an orthopedic fixation system received in the collar.

13. The drill guide of claim 12, wherein the bore is dimensioned to receive a drill or a depth gauge.

14. The drill guide of claim 12, further comprising:
a fastener with a recess and a threaded end adapted to mate with internal threads in an aperture of the guide frame; and
a biasing element adjacent the second end of the connector and wherein the recess of the fastener may receive a portion of the biasing element.

15. The drill guide of claim 14, wherein tightening the fastener adjusts tension in the biasing element, thereby affecting movement of the second end of the connector.

16. The drill guide of claim 12, wherein the collar is dimensioned to move linearly, rotationally, or linearly and rotationally about the bar of the orthopedic fixation system.

17. The drill guide of claim 12, further comprising a tissue sleeve integrally formed in the guide frame.

18. The drill guide of claim 12, further comprising a handle extending from the guide frame.

19. The drill guide of claim 12, wherein the bore is dimensioned to receive a tissue sleeve including a channel through which a fixation element may be inserted.

20. The drill guide of claim 12, wherein the collar is adapted to receive the portion of the orthopedic fixation system from a direction generally perpendicular to the longitudinal axis of the portion of the orthopedic fixation system.

21. The drill guide of claim 12, wherein the collar defines a channel.

22. A drill guide comprising:
a collar frame with a collar defining a channel dimensioned to receive a bar of an orthopedic fixation system from a direction generally perpendicular to the longitudinal axis of the bar;
a guide frame including a bore through which a fixation element of the orthopedic fixation system may be inserted, the guide frame coupled to the collar frame such that the collar frame and the guide frame may rotate about more than one axis relative to each other;
a connector;
a recess of the collar frame that receives a first end of the connector;
an outer cavity of the guide frame that receives a second end of the connector; and
a stabilizing means.

23. The drill guide of claim 22, wherein the stabilizing means is a handle extending from the guide frame.

24. The drill guide of claim 22, wherein the collar is dimensioned to move linearly, rotationally, or linearly and rotationally about the bar of the orthopedic fixation system.

25. The drill guide of claim 22, wherein the fixation element is a half pin.

26. The drill guide of claim 22, further comprising a tissue sleeve integrally formed in the guide frame.

27. The drill guide of claim 22, wherein the collar frame and the guide frame rotate about three axes relative to each other.

28. The drill guide of claim 22, wherein the bore is dimensioned to receive a drill or a depth gauge.

29. The drill guide of claim 22, wherein the bore is dimensioned to receive a tissue sleeve including a channel through which a fixation element may be inserted.

30. The drill guide of claim 22, wherein the stabilizing means comprises a tissue sleeve.

31. The drill guide of claim 22, wherein the stabilizing means comprises a drill bit.

32. The drill guide of claim 22, wherein the stabilizing means comprises a fixation element.

33. An external fixation system comprising:
a plurality of fixation components;
a plurality of fixation elements, at least one of the plurality of fixation elements for use between two fixation components and at least one of the plurality of fixation elements for use between a fixation component and a patient's bone;
a drill guide comprising:
a collar frame with a collar that receives and moves linearly or rotationally about the at least one fixation element for use between two fixation components;
a guide frame including a bore through which one of the at least one fixation elements for use between a fixation component and a patient's bone may be inserted, the guide frame coupled to the collar frame by a ball or pivot joint;
a connector;
a recess of the collar frame adapted to couple to a first end of the connector;
an outer cavity of the guide frame adapted to receive a second end of the connector;
a fastener with a recess and a threaded end adapted to mate with internal threads in an aperture of the guide frame; and
a biasing element adjacent the second end of the connector and wherein the recess of the fastener may receive a portion of the biasing element.

34. The system of claim 33, wherein a collar is dimensioned to move linearly about the portion of the fixation system.

35. The system of claim 33, wherein a collar is dimensioned to move rotationally about the portion of the fixation system.

36. The system of claim 33, wherein the plurality of fixation elements comprises at least one bar.

37. The system of claim 33, wherein the plurality of fixation elements comprises at least one wire.

38. The system of claim 33, wherein the plurality of fixation element comprises at least one ring.

39. An external fixation system comprising:
a plurality of fixation elements;
a plurality of fixation components comprising:
   a first capture member adapted to capture an element of an orthopedic fixation system; and
   a second capture member adapted to capture an element of an orthopedic fixation system and coupled to the first capture member such that the coupling allows the first capture member and the second capture member to rotate about three axes relative to each other; and
a drill guide comprising:
   a collar frame with a collar adapted to receive a portion of an orthopedic fixation system; and
   a guide frame including a bore through which an element of the orthopedic fixation system may be inserted, the guide frame coupled to the collar frame such that the coupling allows the collar frame and the guide frame to rotate about three axes relative to each other.

40. The system of claim 39, wherein the collar may be moved linearly about the portion of the orthopedic fixation system.

41. The system of claim 39, wherein the collar may be moved rotationally about the portion of the orthopedic fixation system.

42. The system of claim 39, wherein first capture member is adapted to receive a bar and the second capture member is adapted to receive a pin.

43. The system of claim 39, wherein the collar frame is adapted to receive a bar and the guide frame is adapted to receive a pin.

44. The system of claim 39, further comprising a tissue sleeve that may be inserted through the bore and including a channel through which an element of an orthopedic fixation system may be inserted.

45. The system of claim 39, wherein the collar is dimensioned to move linearly and rotationally about the portion of the orthopedic fixation system.

46. The system of claim 39, wherein the bore is dimensioned to receive a drill or a depth gauge.

47. The system of claim 39, further comprising a handle extending from the guide frame.

48. The system of claim 39, wherein the collar is adapted to receive the portion of the orthopedic fixation system from a direction generally perpendicular to the longitudinal axis of the portion of the orthopedic fixation system.

49. The system of claim 39, wherein the second capture member is adapted to capture an element of an orthopedic fixation system by snapping onto the element from a direction generally perpendicular to the longitudinal axis of the element.

50. The system of claim 39, wherein the first capture member is adapted to capture an element of an orthopedic fixation system by snapping onto the element from a direction generally perpendicular to the longitudinal axis of the element.

51. An external fixation system comprising:
a plurality of fixation elements;
a plurality of fixation components comprising:
   a first capture member adapted to capture an element of an orthopedic fixation system; and
   a second capture member adapted to capture an element of an orthopedic fixation system and coupled to the first capture member such that the coupling allows the first capture member and the second capture member to rotate about three axes relative to each other; and
a drill guide comprising a collar frame and a guide frame, the guide frame coupled to the collar frame such that the coupling allows the collar frame and the guide frame to rotate about three axes relative to each other.

52. The system of claim 51, wherein a portion of the collar frame is dimensioned to move linearly, rotationally, or linearly and rotationally about a portion of an orthopedic fixation system.

53. The system of claim 51, wherein first capture member is adapted to receive a bar and the second capture member is adapted to receive a pin.

54. The system of claim 51, wherein the collar frame is adapted to receive a bar and the guide frame is adapted to receive a pin.

55. The system of claim 51, further comprising a tissue sleeve that may be inserted through a bore in the guide frame and including a channel through which an element of an orthopedic fixation system may be inserted.

56. The system of claim 51, wherein the guide frame comprises a bore is dimensioned to receive a drill or a depth gauge.

57. The system of claim 51, wherein the guide frame comprises a handle.

58. The system of claim 51, wherein the collar frame is adapted to receive a portion of an orthopedic fixation system from a direction generally perpendicular to the longitudinal axis of the portion of the orthopedic fixation system.

59. The system of claim 51, wherein the second capture member is adapted to capture an element of an orthopedic fixation system by snapping onto the element from a direction generally perpendicular to the longitudinal axis of the element.

60. The system of claim 51, wherein the first capture member is adapted to capture an element of an orthopedic fixation system by snapping onto the element from a direction generally perpendicular to the longitudinal axis of the element.

* * * * *